(12) United States Patent
Janssen et al.

(10) Patent No.: US 7,041,367 B2
(45) Date of Patent: May 9, 2006

(54) GLOVE HAVING IMPROVED DONNING CHARACTERISTICS

(75) Inventors: Robert A. Janssen, Alpharetta, GA (US); Martin S. Shamis, Alpharetta, GA (US); William E. Conley, Alpharetta, GA (US); Maris Vistins, Alpharetta, GA (US); Sanford E. White, Kennesaw, GA (US); Kermit R. Littleton, Elijay, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/454,699

(22) Filed: Jun. 3, 2003

(65) Prior Publication Data
US 2004/0247910 A1 Dec. 9, 2004

(51) Int. Cl.
*B32B 27/08* (2006.01)
*B32B 27/30* (2006.01)
*C08J 7/04* (2006.01)

(52) U.S. Cl. .............. 428/341; 2/161.7; 2/161.8; 2/167; 2/168; 428/451; 428/494; 428/517; 428/519; 428/520

(58) Field of Classification Search ............. 2/161.7, 2/161.8, 167, 168; 428/341, 451, 494, 517, 428/519, 520
See application file for complete search history.

(56) References Cited

U.S. PATENT DOCUMENTS

| | | | |
|---|---|---|---|
| 3,411,982 A | 11/1968 | Kavalir et al. | |
| 3,740,262 A | 6/1973 | Agostinelli | |
| 3,992,221 A | 11/1976 | Homsy et al. | |
| 4,082,862 A * | 4/1978 | Esemplare et al. | 427/133 |
| 4,310,928 A | 1/1982 | Joung | |
| 4,597,108 A | 7/1986 | Momose | |
| 4,851,266 A | 7/1989 | Momose et al. | |
| 5,112,900 A | 5/1992 | Buddenhagen et al. | |
| 5,331,027 A | 7/1994 | Whitbourne | 524/37 |
| 5,395,666 A | 3/1995 | Brindle | 428/323 |
| 5,407,715 A | 4/1995 | Buddenhagen et al. | |
| 5,792,531 A | 8/1998 | Littleton et al. | |
| 6,638,587 B1 | 10/2003 | Wang et al. | 428/35.7 |

FOREIGN PATENT DOCUMENTS

WO WO 00/09320 2/2000

OTHER PUBLICATIONS

ASTM D5712-95, "Standard Test Method for Analysis of Protein in Natural Rubber and Its Products", Apr. 1995, pp. 302-306.
MSDS No.: DRSL0010, "Material Safety Data Sheet", retrieved and printed from the internet Nov. 5, 2004.

* cited by examiner

*Primary Examiner*—D. S. Nakarani
(74) *Attorney, Agent, or Firm*—Dana E. Stano; Vincent T. Kung

(57) ABSTRACT

An elastomeric article includes a substrate body formed from an elastomeric material. The substrate body has a first surface, and a donning layer overlying at least a portion of the first surface. The donning layer is formed from a modified vinyl acetate polymer.

19 Claims, 6 Drawing Sheets

GLOVE HAVING IMPROVED DONNING CHARACTERISTICS

BACKGROUND OF THE INVENTION

Tightly fitting elastomeric articles, such as surgical and examination gloves, may be difficult to don due to blocking, the tendency of the glove elastomer to stick to itself. As a result, gloves often contain a powdered lubricant on the surface that contacts the skin of the wearer to facilitate donning. Most commonly, epichlorohydrin treated crosslinked cornstarch is dusted on the inside surface of the glove during manufacturing. While use of cornstarch does improve the donning characteristics of the glove, it may not be feasible for all applications. One such situation is the use of powders for surgical glove applications. If some of the powder inadvertently enters the surgical site, it may cause complications for the patient. For instance, the powder may carry an infectious agent or the patient may be allergic to the powder.

Other techniques may be used to improve the donning characteristics of surgical and examination gloves. These techniques include, for example, manufacturing the glove from a modified latex, using an inner layer of a hydrophilic polymer, providing lubricating particles on the inner surface of the glove, and the like. However, as some degree of blocking may occur with these techniques, there remains a need for a glove with improved donning characteristics.

SUMMARY OF THE INVENTION

The present invention generally relates to an elastomeric article, such as a glove or a condom, that may be readily donned without the use of powders.

The article includes a substrate body formed from an elastomeric material, the substrate body having a first surface, and a donning layer formed from a modified vinyl acetate polymer overlying at least a portion of the first surface. Any elastomeric material may be used to form the substrate body, and in some instances, the substrate body may be formed from a natural rubber or a nitrite butadiene rubber. The modified vinyl acetate polymer may be silicone-modified.

The present invention further relates to an elastomeric article including a substrate body formed from an elastomeric material, the substrate body having a first surface, a donning layer formed from a silicone-modified vinyl acetate polymer overlying at least a portion of the first surface, and a lubricant layer overlying at least a portion of the donning layer. The silicone-modified vinyl acetate polymer may contain from about 15 atomic % to about 30 atomic % silicon. The lubricant layer may be formed from a quaternary ammonium compound and a silicone emulsion.

The present invention also relates to a method of preparing an elastomeric article. The method includes preparing a substrate body from an elastomeric material, the substrate body having a first surface, and forming, a donning layer from a modified vinyl acetate polymer over at least a portion of the first surface. The method contemplates curing the elastomeric material before forming the donning layer. The method also contemplates curing the elastomeric material after forming the donning layer. The method further contemplates forming a lubricant layer over at least a portion of the donning layer, where the lubricant layer includes a silicone emulsion.

DESCRIPTION OF THE INVENTION

The present invention generally relates to an elastomeric article, such as a condom or glove, and a method of forming such an elastomeric article. As used herein, the term "elastomeric article" refers to an article formed predominantly from an elastomeric material. As used herein, the term "elastomeric material" refers to a polymeric material that is capable of being easily stretched or expanded, and will substantially return to its previous shape upon release of the stretching or expanding force.

An article made according to the present invention features improved donning characteristics without the use of powders. The article includes a donning layer formed from a silicone-modified vinyl acetate polymer. This provides a significant advantage over powder-coated articles, which require additional processing steps to remove excess powder and are not suitable for some applications, such as surgical gloves.

Figure 1:
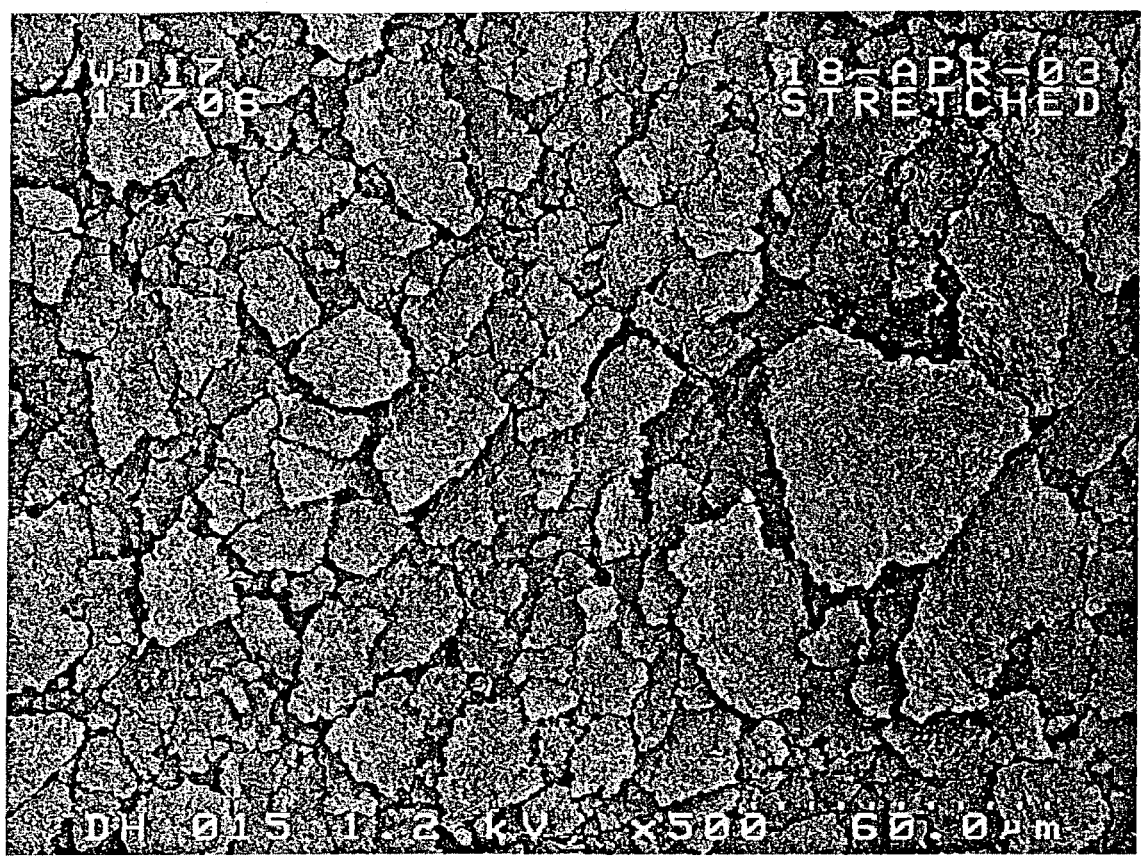
FIG. 1 is a scanning electron micrograph of the donning layer on a glove formed according to the present invention.

Furthermore, while some donning layer polymers have been traditionally selected to have elastomeric characteristics so that the donning layer is able to stretch and recover in concert with the substrate body without peeling away or flaking off, it has been discovered that the glove of the present invention is able to provide a non-elastomeric donning layer that does not flake off, even under the stress of being stretched and deformed. While not wishing to be bound by any particular theory, it is believed that the donning layer polymer develops microscopic fractures in the polymer layer when the glove is exposed to a stretching force. FIG. 1 is a scanning electron micrograph of the donning layer of the present invention after being subjected to a stretching force and allowing the glove to retract. Despite the generation of such fractures, it has been demonstrated that the donning layer formed from a silicone-modified vinyl acetate polymer does not flake or chip off the article. Thus, beneficial donning characteristics are obtained from a non-elastomeric polymer without the use of powders.

Figure 2:
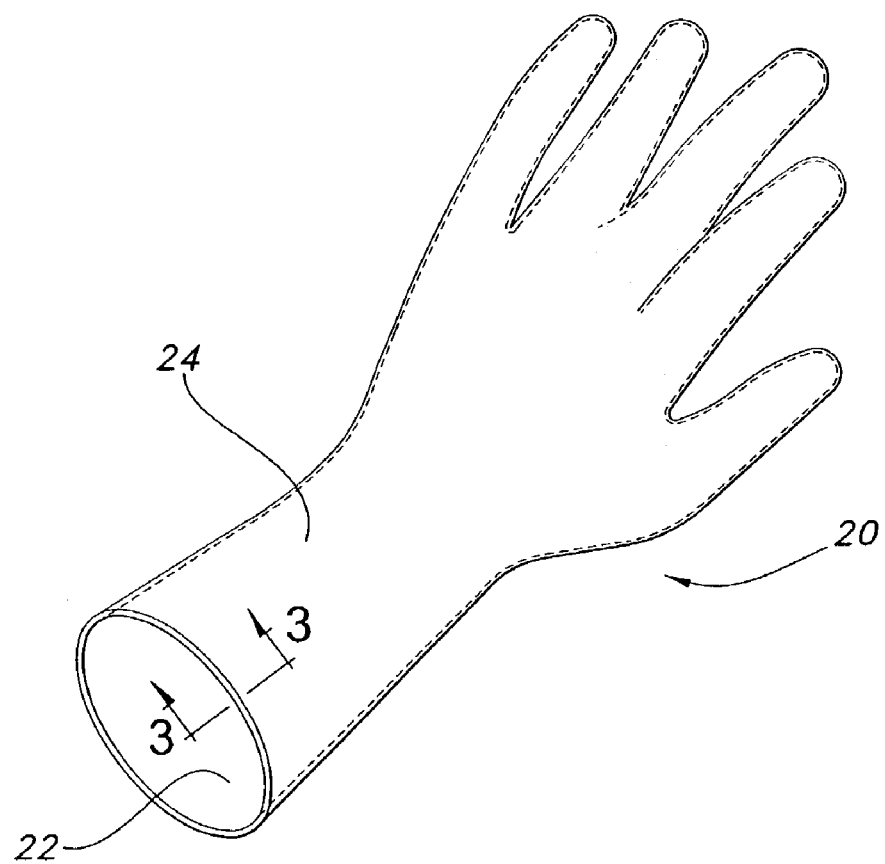
FIG. 2 is a perspective view of an elastomeric article, namely a glove, according to the present invention.
Figure 3A:
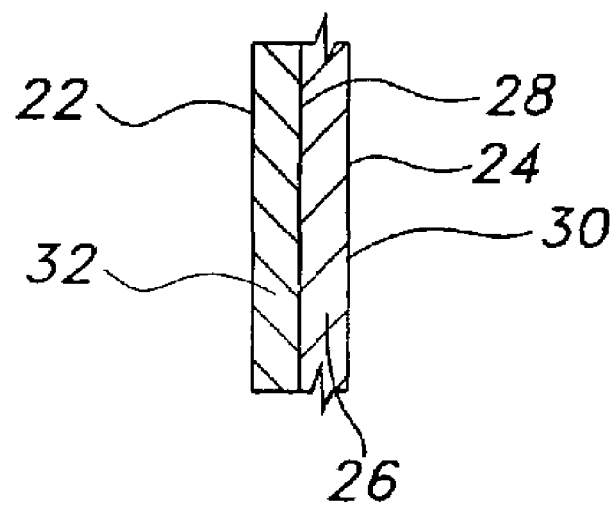
FIG. 3A is a schematic cross-sectional illustration the article of FIG. 2 taken along a line 3—3, the article including a substrate body and a donning layer.
Figure 3B:
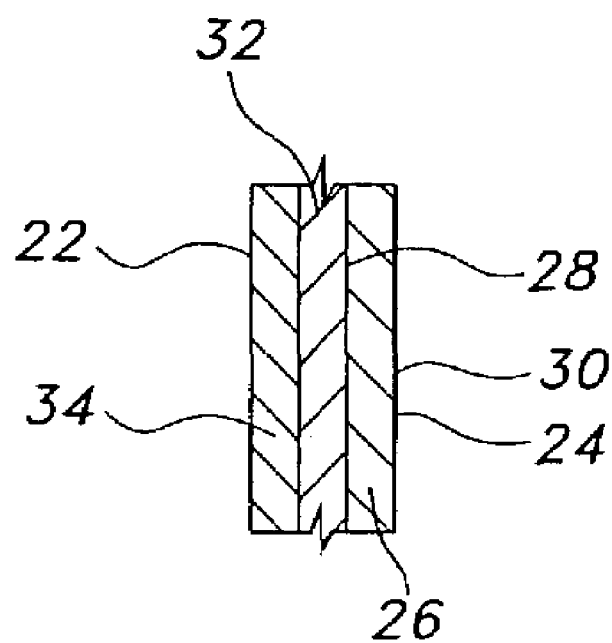
FIG. 3B is another schematic cross-sectional illustration the article of FIG. 2 taken along a line 3—3, the article including a substrate body, a donning layer, and a lubricant layer.

An article made according to the present invention features, for example, a glove 20, generally includes an inside surface 22 and an outside surface 24 (FIG. 2). As used herein, the "inside surface" refers to the surface of the article that contacts the body of the wearer. As used herein, the "outside surface" refers to the surface of the article that is distal from the body of the wearer. The glove includes a substrate body 26 having a first surface 28 and a second surface 30 (FIGS. 3A–3B). As used herein, "first surface" refers to the surface of the substrate body proximal to the body of the wearer. As used herein, "second surface" refers to the surface of the substrate body distal to the body of the wearer.

The article of the present invention may include a single layer or multiple layers as desired. In a single layer glove including only the substrate body, the first surface may form the inside surface of the glove. However, in a multi-layer glove having additional layers proximal the body of the wearer, the additional layer or layers may each form a portion of the inside surface, or the entire inside surface, as desired. Likewise, in a single layer glove including only the substrate body, the second surface may form the outside surface of the glove. However, in a multi-layer glove having additional layers distal from the body of the wearer, the additional layer or layers may each form a portion of the outside surface, or the entire outside surface, as desired.

For example, as depicted in FIG. 3A, the article may include a donning layer 32 overlying at least a portion of the first surface 28 of the substrate body 26. In such an article, the donning layer 32 forms at least a portion of the inside surface 22 of the glove 20. As depicted in FIG. 3B, the article may also include other layers, such as a lubricant layer 34 that overlies at least a portion of the donning layer 32. In such an article, the lubricant layer 34 forms at least a portion of the inside surface 22 of the glove 20.

The substrate body 26 (FIGS. 3A–3B) may be formed from any suitable elastomeric material, and in some embodiments, the substrate body may be formed from natural rubber, which is typically provided as a natural rubber latex. In other embodiments, the elastomeric material may include nitrile butadiene rubber, and in particular, may include carboxylated nitrile butadiene rubber. While articles formed from natural rubber and nitrile rubber are described in detail herein, it should be understood that any other suitable polymer or combination of polymers may be used with the present invention. For instance, the substrate body may be formed from a styrene-ethylene-butylene-styrene (S-EB-S) block copolymer. In some embodiments, the body may be formed from two or more elastomeric materials. For instance, the body may be formed from two or more S-EB-S block copolymers, such as those described in U.S. Pat. Nos. 5,112,900 and 5,407,715 to Buddenhagen et al., both incorporated herein by reference in their entirety. In other embodiments, the elastomeric material may include a styrene-isoprene-styrene block copolymer, styrene-butadiene-styrene block copolymer, styrene-isoprene block copolymer, styrene-butadiene block copolymer, synthetic isoprene, chloroprene rubber, polyvinyl chloride, silicone rubber, or a combination thereof.

The donning layer 32 (FIGS. 3A–3B) may be formed from any polymer that facilitates donning and generally includes a modified vinyl acetate polymer. In some embodiments, the vinyl acetate polymer may be silicone-modified. As used herein, the term "silicone" generally refers to a broad family of synthetic polymers that have a repeating silicon-oxygen backbone, including, but not limited to, polydimethylsiloxane and polysiloxanes having hydrogen-bonding functional groups selected from the group consisting of amino, carboxyl, hydroxyl, ether, polyether, aldehyde, ketone, amide, ester, and thiol groups. The silicone-modified vinyl acetate polymer may include any suitable silicon content, and in some instances, the silicone-modified vinyl acetate polymer may include from about 10 atomic % to about 30 atomic % silicon. In other instances, the silicone-modified vinyl acetate polymer may include from about 15 atomic % to about 25 atomic % silicon. In yet other instances, the silicone-modified vinyl acetate polymer may include from about 17 atomic % to about 22 atomic % silicon. In one such embodiment, the silicone-modified vinyl acetate polymer may include about 17.7 atomic % silicon. In another such embodiment, the silicone-modified vinyl acetate polymer may include about 21.8 atomic % silicon.

One such modified vinyl acetate polymer that may be suitable for use with the present invention is commercially available from Reichhold Chemicals, Inc. (Research Triangle Park, N.C.) under the trade name SYNTHEMUL® 97907-00 synthetic resin emulsion. SYNTHEMUL® 97907-00 synthetic resin emulsion is believed to be a carboxylated vinyl acetate latex that contains about 46 mass % modified vinyl acetate polymer, about 56 mass % water, and small amounts of vinyl acetate monomer. Another modified vinyl acetate polymer that may be suitable for use with the present invention is also commercially available from Reichhold Chemicals, Inc. (Research Triangle Park, N.C.) under the trade name SYNTHEMUL® 97635-00 synthetic resin emulsion. SYNTHEMUL® 97635-00 synthetic resin emulsion is believed to be a vinyl acetate homopolymer that contains about 46 mass % vinyl acetate homopolymer, about 56 mass % water, and small amounts of vinyl acetate monomer. While exemplary modified vinyl acetate polymers are set forth herein, it should be understood that any suitable modified vinyl acetate polymer may be used with the present invention.

The article of the present invention may include a lubricant layer 34 overlying at least a portion of the donning layer 32 to further facilitate donning (FIG. 3B). In one embodiment, the lubricant layer may contain a silicone or silicone-based component. In some embodiments, polydimethylsiloxane and/or modified polysiloxanes may be used as the silicone component in accordance with the present invention. For instance, some suitable modified polysiloxanes that can be used in the present invention include, but are not limited to, phenyl-modified polysiloxanes, vinyl-modified polysiloxanes, methyl-modified polysiloxanes, fluoro-modified polysiloxanes, alkyl-modified polysiloxanes, alkoxy-modified polysiloxanes, amino-modified polysiloxanes, and combinations thereof.

In some embodiments, the lubricant layer may include a silicone emulsion. One such silicone emulsion that may be suitable for use with the present invention is DC 365, a pre-emulsified silicone (35% TSC) that is commercially available from Dow Corning Corporation (Midland, Mich.). DC 365 is believed to contain 40–70 mass % water (aqueous solvent), 30–60 mass % methyl-modified polydimethylsiloxane (silicone), 1–5 mass % propylene glycol (non-aqueous solvent), 1–5 mass % polyethylene glycol sorbitan monolaurate (nonionic surfactant), and 1–5 mass % octylphenoxy polyethoxy ethanol (nonionic surfactant). Another silicone emulsion that may be suitable for use with the present invention is SM 2140, commercially available from GE Silicones (Waterford, N.Y.). SM 2140 is a pre-emulsified silicone (50% TSC) that is believed to contain 30–60 mass % water (aqueous solvent), 30–60 mass % amino-modified polydimethylsiloxane (silicone), 1–5% ethoxylated nonyl phenol (nonionic surfactant), 1–5 mass % trimethyl-4-nonyloxypolyethyleneoxy ethanol (nonionic surfactant), and minor percentages of acetaldehyde, formaldehyde, and 1,4 dioxane. Another silicone emulsion that may be suitable for use with the present invention is SM 2169 available from GE Silicones (Waterford, N.Y.). SM 2169 is a pre-emulsified silicone that is believed to contain 30–60 mass % water, 60–80 mass % polydimethylsiloxane, 1–5 mass % polyoxyethylene lauryl ether, and a small amount of formaldehyde. Yet another silicone that may be suitable for use with the present invention is commercially available from GE Silicones (Waterford, N.Y.) under the trade name AF-60. AF-60 is believed to contain polydimethylsiloxane, acetylaldehyde, and small percentages of emulsifiers. If desired, these pre-emulsified silicones may be diluted with water or other solvents prior to use.

In another embodiment, the lubricant layer may contain a quaternary ammonium compound, such as that commercially available from Goldschmidt Chemical Corporation of Dublin, Ohio under the trade name VERISOFT® BTMS. VERISOFT® BTMS is believed to contain behnyl trimethyl sulfate and cetyl alcohol. Thus for example, in one embodiment, the lubricant layer includes a quaternary ammonium compound such as VERISOFT® BTMS and a silicone emulsion such as SM 2169.

In other embodiments, the lubricant layer may include, for example, a cationic surfactant (e.g., cetyl pyridinium chloride), an anionic surfactant (e.g., sodium lauryl sulfate), a nonionic surfactant, or the like.

In some embodiments, one or more cationic surfactants may be used. Examples of cationic surfactants that may be suitable for use with the present invention include, for example, behenetrimonium methosulfate, distearyldimonium chloride, dimethyl dioctadecyl ammonium chloride, cetylpyridinium chloride, methylbenzethonium chloride, hexadecylpyridinium chloride, hexadecyltrimethylammonium chloride, benzalkonium chloride, dodccylpyridinium chloride, the corresponding bromides, hydroxyethylheptadecylimidazolium halides, coco aminopropyl betaine, and coconut alkyldimethylammonium betaine. Additional cationic surfactants that may be used include methyl bis (hydrogenated tallow amidoethyl)-2-hydroxyethly ammonium methyl sulfate, methyl bis(tallowamido ethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, methyl bis(hydrogenated tallowamido ethyl)-2-hydrogenated tallow imidazolinium methyl sulfate, methyl bis(ethyl tallowate)-2-hydroxyethyl ammonium methyl sulfate, methyl bis(ethyl tallowate)-2-hydroxyethyl ammonium methyl sulfate, dihydrogenated tallow dimethyl ammonium chloride, didecyl dimethyl ammonium chloride, dioctyl dimethyl ammonium chloride, octyl decyl dimethyl ammonium chloride diamidoamine ethoxylates, diamidoamine imidazolines, and quaternary ester salts.

In some embodiments, one or more nonionic surfactants may be used. Nonionic surfactants typically have a hydrophobic base, such as a long chain alkyl group or an alkylated aryl group, and a hydrophilic chain comprising a certain number (e.g., 1 to about 30) of ethoxy and/or propoxy moieties. Examples of some classes of nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$–$C_{18}$) acids, condensation products of ethylene oxide with long chain amines or amides, condensation products of ethylene oxide with alcohols, and mixtures thereof.

Specific examples of suitable nonionic surfactants include, but are not limited to, methyl gluceth-10, PEG-20 methyl glucose distearate, PEG-20 methyl glucose sesquistearate, $C_{11}$–$_{15}$ pareth-20, ceteth-8, ceteth-12, dodoxynol-12, laureth-15, PEG-20 castor oil, polysorbate 20, steareth-20, polyoxyethylene 10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, oxyethanol, 2,6,8-trimethyl-4-nonyloxypolyethylene oxyethanol; octylphenoxy polyethoxy ethanol, nonylphenoxy polyethoxy ethanol, 2,6,8-trimethyl-4-nonyloxypolyethylene alkyleneoxypolyethyleneoxyethanol, alkyleneoxypolyethyleneoxyethanol, alkyleneoxypolyethyleneoxyethanol, and mixtures thereof.

Additional nonionic surfactants that may be used include water soluble alcohol ethylene oxide condensates that are the condensation products of a secondary aliphatic alcohol containing between about 8 to about 18 carbon atoms in a straight or branched chain configuration condensed with between about 5 to about 30 moles of ethylene oxide. Such nonionic surfactants are commercially available under the trade name TERGITOL® from Union Carbide Corp. (Danbury, Conn.). Specific examples of such commercially available nonionic surfactants of the foregoing type are $C_{11}$–$C_{15}$ secondary alkanols condensed with either 9 moles of ethylene oxide (TERGITOL® 15-S-9) or 12 moles of ethylene oxide (TERGITOL® 15-S-12) marketed by Union Carbide Corp. (Danbury, Conn.).

Other suitable nonionic surfactants include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of ethylene oxide per mole of nonyl phenol, dinonyl phenol condensed with about 12 moles of ethylene oxide per mole of phenol, dinonyl phenol condensed with about 15 moles of ethylene oxide per mole of phenol and diisoctylphenol condensed with about 15 moles of ethylene oxide per mole of phenol. Commercially available nonionic surfactants of this type include IGEPAL® CO-630 (a nonyl phenol ethoxylate) marketed by ISP Corp. (Wayne, N.J.). Suitable nonionic ethoxylated octyl and nonyl phenols include those having from about 7 to about 13 ethoxy units.

In some embodiments, one or more amphoteric surfactants may be used. One class of amphoteric surfactants that may suitable for use with the present invention includes the derivatives of secondary and tertiary amines having aliphatic radicals that are straight chain or branched, where one of the aliphatic substituents contains from about 8 to 18 carbon atoms and at least one of the aliphatic substituents contains an anionic water-solubilizing group, such as a carboxy, sulfonate, or sulfate group. Some examples of amphoteric surfactants include, but are not limited to, sodium 3-(dodecylamino)-propionate, sodium 3-(dodecylamino)-propane-1-sulfonate, sodium 2-(dodecylamino)ethyl sulfate, sodium 2-(dimethylamino)octadecanoate, disodium 3-(N-carboxymethyl-dodecylamino)propane-1-sulfonate, sodium 1-carboxymethyl-2-undecylimidazole, disodium octadecylnimodiacetate, and sodium N, N-bis (2-hydroxyethyl)-2-sulfato-3-dodecoxypropylamine.

Additional classes of suitable amphoteric surfactants include phosphobetaines and phosphitaines. For instance, some examples of such amphoteric surfactants include, but are not limited to, sodium coconut N-methyl taurate, sodium oleyl N-methyl taurate, sodium tall oil acid N-methyl taurate, cocodimethylcarboxymethylbetaine, lauryldimethylcarboxymethylbetaine, lauryldimethylcarboxyethylbetaine, cetyldimethylcarboxymethylbetaine, sodium palmitoyl N-methyl taurate, oleyldimethylgammacarboxypropylbetaine, lauryl-bis-(2-hydroxypropyl)-carboxyethylbetainc, di-sodium oleamide PEG-2 sulfosuccinate, laurylamido-bis-(2-hydroxyethyl) propylsultaine, lauryl-bis-(2-hydroxyethyl) carboxymethylbetaine, cocoamidodimethylpropylsultaine, stearylamidodimethylpropylsultaine, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamido propyl monosodium phosphitaine, lauric myristic amido propyl monosodium phosphitaine, cocoanmdo disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamphoglycinate, cocoamphocarboxyglycinate, capryloamphocarboxyglycinate, lauroamphocarboxyglycinate, lauroamphoglycinate, capryloamphocarboxypropionate, lauroamphocarboxypropionate, cocoamphopropionate, cocoamphocarboxypropionate, dihydroxyethyl tallow glycinate, and mixtures thereof.

In certain instances, one or more anionic surfactants may be used. Suitable anionic surfactants include, but are not limited to, alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkyllauryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof.

Particular examples of some suitable anionic surfactants include, but are not limited to, $C_8$–$C_{18}$ alkyl sulfates, $C_8$–$C_{18}$ fatty acid salts, $C_8$–$C_{18}$ alkyl ether sulfates having one or two moles of ethoxylation, $C_8$–$C_{18}$ alkamine oxides, $C_8$–$C_{18}$ alkoyl sarcosinates, $C_8$–$C_{18}$ sulfoacetatcs, $C_8$–$C_{18}$ sulfosuccinates, $C_8$–$C_{18}$ alkyl diphenyl oxide disulfonates, $C_8$–$C_{18}$ alkyl carbonates, $C_8$–$C_{18}$ alpha-olefin sulfonates, methyl ester sulfonates, and blends thereof. The $C_8$–$C_1$–8 alkyl group may be straight chain (e.g., lauryl) or branched (e.g., 2-ethylhexyl). The cation of the anionic surfactant may be an alkali metal (e.g., sodium or potassium), ammonium, $C_1$–$C_4$ alkylammonium (e.g., mono-, di-, tri), or $C_1$–$C_3$ alkanolammonium (e.g., mono-, di-, tri).

Specific examples of such anionic surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, ricinoleates, cetyl sulfates, and so forth.

The article of the present invention may be formed using a variety of processes, for example, dipping, spraying, tumbling, drying, and curing. An exemplary dipping process for forming a glove is described herein, though other processes may be employed to form various articles having different shapes and characteristics. For example, a condom may be formed in substantially the same manner, although some process conditions may differ from those used to form a glove. Furthermore, it should be understood that a batch, semi-batch, or a continuous process may be used with the present invention.

A glove is formed on a hand-shaped mold, termed a "former". The former may be made from any suitable material, such as glass, metal, porcelain, or the like. The surface of the former defines at least a portion of the surface of the glove to be manufactured.

In general, the glove is formed by dipping the former into a series of compositions as needed to attain the desired glove characteristics. The glove may be allowed to solidify between layers. Any combination of layers may be used, and although specific layers are described herein, it should be understood that other layers and combinations of layers may be used as desired.

Where a coagulant based process is used, as in the case of forming a natural rubber glove, the former is first conveyed through a preheated oven to evaporate any water present from cleaning the former. The former is then dipped into a bath typically containing a coagulant, a powder source, a surfactant, and water. The residual heat evaporates the water in the coagulant mixture leaving, for example, calcium nitrate, calcium carbonate powder, and surfactant on the surface of the former. The coagulant may contain calcium ions (e.g., calcium nitrate) that enable a polymer latex, for example, a natural rubber latex or a nitrile rubber latex, to deposit onto the former. The powder may be calcium carbonate powder, which aids release of the completed glove from the former. The surfactant provides enhanced wetting to avoid forming a meniscus and trapping air between the form and deposited latex, particularly in the cuff area. However, any suitable coagulant composition may be used, including those described in U.S. Pat. No. 4,310,928 to Joung, incorporated herein in its entirety by reference.

The coated former is then dipped into a latex containing an elastomeric material that forms the substrate body. In some embodiments, the elastomeric material includes natural rubber, which may be supplied as a compounded natural rubber latex. Thus, the bath may contain, for example, compounded natural rubber latex, stabilizers, antioxidants, curing activators, organic accelerators, vulcanizers, and the like. The stabilizers may include phosphate-type surfactants. The antioxidants may be phenolic, for example, 2,2'-methylenebis (4-methyl-6-t-butylphenol). The curing activator may be zinc oxide. The organic accelerator may be dithiocarbamate. The vulcanizer may be sulfur or a sulfur-containing compound. To avoid crumb formation, the stabilizer, antioxidant, activator, accelerator, and vulcanizer may first be dispersed into water by using a ball mill and then combined with the natural rubber latex.

During the dipping process, the coagulant on the former causes some of the elastomeric material to become locally unstable and coagulate onto the surface of the former. The elastomeric material coalesces, capturing the particles present in the coagulant composition at the surface of the coagulating elastomeric material. The former is withdrawn from the bath of elastomeric material and the coagulated layer is permitted to fully coalesce, thereby forming the substrate body. The former is dipped into one or more latex baths a sufficient number of times to attain the desired glove thickness. In some embodiments, the substrate body may have a thickness of from about 0.004 inches to about 0.012 inches.

The former is then dipped into a leaching tank in which hot water is circulated to remove the water-soluble components, such as residual calcium nitrates and proteins contained in the natural rubber latex. This leaching process may generally continue for about twelve minutes at a water temperature of about 120° F. The glove is then dried on the former to solidify and stabilize the substrate body. It should be understood that various conditions, process, and materials may be used to form the substrate body.

Other layers may be formed by including additional dipping processes. Such layers may be used to impart additional attributes to the glove. When these processes are complete, the former then undergoes an additional coating process to form the interior, or donning layer of the glove. It should be understood that any process may be used to form the donning layer, such as dipping, spraying, immersion, printing, tumbling or any other suitable technique.

Thus, for example, where a dipping process is used, the former is dipped into a composition that contains the donning layer polymer. In accordance with the present invention, the donning layer composition may include a modified vinyl acetate polymer. More particularly, the composition may include a silicone-modified vinyl acetate, such as that available from Reichhold Chemicals, Inc. under the trade name SYNTHEMUL® 97907-00, provided as a 46 mass % total solids content (TSC) emulsion. In some instances, the donning layer composition may include from about 0.5 mass % TSC to about 6 mass % TSC. In other embodiments, the donning layer composition may include from about 1 mass % TSC to about 5 mass % TSC. In other embodiments, the donning layer composition may include about 4 mass % TSC. In yet other embodiments, the donning layer composition may include about 2 mass % TSC.

The donning layer may be present in the finished elastomeric article any suitable amount, and in some embodiments, the donning layer may be present in an amount of from about 0.1% mass % to about 2.5 mass % of the elastomeric article. In other embodiments, the donning layer may be present in an amount of from about 0.25 mass % to about 1.5 mass % of the elastomeric article. In yet other embodiments, the donning layer may be present in an amount of about 0.5 mass % of the elastomeric article.

When the former is withdrawn from the composition, the substrate body coated with the donning layer composition is then sent to a curing station where the elastomeric material is vulcanized, typically in an oven. The curing station initially evaporates any remaining water in the coating on the former and then proceeds to a higher temperature vulcanization. The drying may occur at a temperature of from about 85° C. to about 95° C., with a vulcanization step occurring at a temperature of from about 110° C. to about 120° C. For example, the glove 20 may be vulcanized in a single oven at a temperature of 115° C. for about 20 minutes. Alternatively, the oven may be divided into four different zones with a former being conveyed through zones of increasing temperature. For instance, the oven may have four zones with the first two zones being dedicated to drying and the second two zones being primarily for vulcanizing. Each of the zones may have a slightly higher temperature, for example, the first zone at about 80° C., the second zone at about 95° C., a third zone at about 105° C., and a final zone at about 115° C. The residence time of the former within each zone may be about ten minutes. The accelerator and vulcanizer contained in the latex coating of the former are used to crosslink the natural rubber. The vulcanizer forms sulfur bridges between different rubber segments and the accelerator is used to promote rapid sulfur bridge formation.

It has been found that use of a modified vinyl acetate polymer, for instance a silicone-modified vinyl acetate polymer, affords a high degree of process flexibility in forming the elastomeric article of the present invention. In particular, it has been found that the donning layer may be formed prior to curing the article, as is described herein, or after the substrate body has been cured, as is described in the Examples.

Furthermore, where a natural rubber glove is being formed, it has been found that, contrary to process requirements of other donning layer polymers, use of a silicone-modified vinyl acetate polymer permits the final leaching step to be performed prior to or after formation of the donning layer. Thus, although a particular exemplary process is described above, it should be understood that use of a silicone-modified vinyl acetate polymer has enabled significant flexibility to be introduced into the process, and that such alternate processes are contemplated by the present invention. While not wishing to be bound to any particular theory, it is believed that the hydrophilic nature of the silicone-modified vinyl acetate polymer may cause the polymer to swell during the leaching process. As the silicone-modified vinyl acetate polymer particles expand, the spaces between the particles increase, thereby enabling the leaching water to flow to the substrate body and carry away excess proteins and chemicals. Alternatively, it is believed that the residual chemicals and proteins may migrate to the second surface of the substrate body and through the donning layer, where the chemicals and proteins are removed during the leaching process.

When all of the desired polymer layers have been formed and the glove is solidified, the former may be transferred to a stripping station where the glove is removed from the former. The stripping station may involve automatic or manual removal of the glove from the former. For example, in one embodiment, the glove is manually removed and turned inside out as it is stripped from the former. Where such a stripping process is used, it is typical to dip the former into a slurry containing calcium carbonate in water prior to proceeding to the stripping station. The former is then exposed to air to evaporate the water, leaving calcium carbonate particles on the surface of the donning layer. This enables the glove to roll over itself as it is stripped from the former without sticking to itself. Where such a slurry is used, the excess calcium carbonate is then removed during subsequent processing. Contrary to such typical instances, it has been discovered that no such slurry dip is needed to enable the glove of the present invention to be removed from the former. The silicone-modified vinyl acetate polymer donning layer of the present invention is sufficiently non-tacky to be easily stripped from the former. This creates a significant advantage over gloves that must be subjected to cumbersome rinsing and drying steps to remove the calcium carbonate to create a "powder-free" glove.

Nonetheless, the solidified glove may then undergo to various post-formation processes. In some instances, the glove may be inverted as needed to expose the donning layer for halogenation. The halogenation (e.g., chlorination) may be performed in any suitable manner known to those skilled in the art. Chlorination generally entails contacting the surface to be chlorinated to a source of chlorine. Such methods include: (1) direct injection of chlorine gas into a water mixture, (2) mixing high density bleaching powder and aluminum chloride in water, (3) brine electrolysis to produce chlorinated water, and (4) acidified bleach. Examples of such methods are described in U.S. Pat. No. 3,411,982 to Kavalir; U.S. Pat. No. 3,740,262 to Agostinelli; U.S. Pat. No. 3,992,221 to Homsy, et al.; U.S. Pat. No. 4,597,108 to Momose; and U.S. Pat. No. 4,851,266 to Momose, U.S. Pat. No. 5,792,531 to Littleton, et al., which are incorporated herein in their entirety by reference. In one embodiment, for example, chlorine gas is injected into a water stream and then fed into a chlorinator (a closed vessel) containing the glove. The concentration of chlorine can be altered to control the degree of chlorination. The chlorine concentration is typically at least about 100 parts per million (ppm), in some embodiments from about 200 ppm to about 3500 ppm, and in some embodiments, from about 300 ppm to about 600 ppm, for example, about 400 ppm. The duration of the chlorination step may also be controlled to vary the degree of chlorination and may range, for example, from about 1 to about 10 minutes, for example, 4 minutes.

Still within the chlorinator, the chlorinated glove may then be rinsed with tap water at about room temperature. This rinse cycle may be repeated as necessary. Once all water is removed, the glove is tumbled to drain the excess water.

A lubricant composition may then be added into the chlorinator and tumbled for about five minutes. The lubricant forms a lubricant layer on at least a portion of the donning layer to further enhance donning of the glove. Any suitable lubricant may be used with the present invention as described herein. One such lubricant may include a quaternary ammonium compound such as VERISOFT® BTMS and a silicone emulsion such as SM 2169.

The lubricant solution is then drained from the chlorinator and may be reused if desired. It should be understood that the lubricant composition may be applied at a later stage in the forming process, and may be applied using any technique, such as dipping, spraying, immersion, printing, tumbling, or the like. The coated glove is then put into a drier and dried for about 10 to 60 minutes (e.g., 40 minutes) at from about 20° C. to about 80° C. (e.g., 40° C.) to dry the inside surface of the glove. The glove is then inverted and the outside surface may be dried for about 20 to 100 minutes (e.g., 60 minutes) at from about 20° C. to about 80° C. (e.g., 40° C.).

These discoveries are evidenced by the following examples, which are not intended to be limiting in any manner.

EXAMPLES 1–3

The ability to form a natural rubber article according to the present invention was demonstrated. In each instance, several glove formers were cleaned and dried. The formers were then dipped into a coagulant composition containing calcium nitrate, a surfactant, and other components. The coagulant on each former was then dried for about 35 seconds at a temperature of about 105° C., and then for about 35 seconds at a temperature of about 75° C.

The formers were then dipped into a 30 mass % high ammonia natural rubber latex composition to form the substrate body of each glove. The formers were then exposed to air to permit the substrate body to solidify on the surface of each former. The formers were exposed to air at a temperature of about 105° C. for about 65 seconds, then to air at a temperature of about 110° C. for about 35 seconds.

The substrate body on the former was then leached in circulating water at a temperature of about 45° C. for about 2 minutes to remove any residual proteins and coagulant chemicals.

EXAMPLE 1

In this instance, the donning layer was formed over the substrate body prior to curing the natural rubber.

After forming the substrate body as described above, the formers were then dipped into a composition to form the donning layer. The composition included about 2 mass % SYNTHEMUL® 97907-00 silicone-modified vinyl acetate polymer in deionized water.

Each former was then sent to a bead rolling station where a bead was formed on the cuff of each glove. The polymer on the formers was then dried for about 67 seconds at a temperature of about 110° C.

The formers were then sent to a curing station having multiple temperature zones to vulcanize and solidify the natural rubber substrate body and the donning layer. The total amount of time required to cure the article was about 30 minutes. The gloves still on the formers were then leached in circulating water at a temperature of about 40° C. for about 2 minutes to remove residual proteins and chemicals. The gloves were then dried for about 67 seconds at a temperature of 110° C. and stripped from the formers.

The gloves were then donned to evaluate the efficacy of the silicone-modified vinyl acetate donning layer and found to be readily donned without the use of powder.

EXAMPLE 2

The ability to form an article according to the present invention was demonstrated. In this instance, the donning layer was formed over the substrate body after curing the natural rubber.

After forming the substrate body as described above, the formers were then sent to a curing station having multiple temperature zones to vulcanize and solidify the natural rubber substrate body and the donning layer. The total amount of time required to cure the article was about 30 minutes. The gloves still on the formers were then leached in circulating water at a temperature of about 40° C. for about 2 minutes to remove any residual proteins and chemicals. The gloves were then dried for about 67 seconds at a temperature of about 110° C.

The formers were then dipped into a composition to form the donning layer. The composition included about 4 mass % SYNTHEMUL® 97907-00 silicone-modified vinyl acetate polymer in deionized water.

Each former was then sent to a bead rolling station where a bead was formed on the cuff of each glove. The polymer on the formers was then dried for about 67 seconds at a temperature of about 110° C. The gloves were then stripped from the formers.

The gloves were then donned to evaluate the efficacy of silicone-modified vinyl acetate donning layer and found to be readily donned without the use of powder.

EXAMPLE 3

The ability to form an article according to the present invention was demonstrated. In this instance, the donning layer was formed over the substrate body after curing the natural rubber. Also, the final leaching step was performed after formation of the donning layer to evaluate the flexibility of the process.

After forming the substrate body as described above, the formers were then sent to a curing station having multiple temperature zones to vulcanize and solidify the natural rubber substrate body and the donning layer. The total amount of time required to cure the article was about 30 minutes.

The formers were then dipped into a composition to form the donning layer. The composition included about 4 mass % SYNTHEMUL® 97907-00 silicone-modified vinyl acetate polymer in deionized water. The gloves were then dried for about 67 seconds at a temperature of about 110° C. The gloves still on the formers were then leached in circulating water at a temperature of about 40° C. for about 2 minutes to remove any residual proteins and chemicals.

Each former was then sent to a bead rolling station where a bead was formed on the cuff of each glove. The polymer on the formers was then dried for about 67 seconds at a temperature of about 110° C. The gloves were then stripped from the formers.

The gloves were then donned to evaluate the efficacy of silicone-modified vinyl acetate donning layer and found to be readily donned without the use of powder.

EXAMPLES 4–6

The impact of leaching at various points in the natural rubber glove formation process was determined. In each of Examples 4–6, 135 glove formers were cleaned and dried. The formers were then dipped into a coagulant composition containing calcium nitrate, a surfactant, and other components. The coagulant on each former was then dried for about 35 seconds at a temperature of about 105° C., and then for about 35 seconds at a temperature of about 75° C.

The formers were then dipped into a 30 mass % high ammonia natural rubber latex composition to form the substrate body of each glove. The formers were then exposed to air to permit the elastomeric material to form a film on the surface of each former. The formers were exposed to air at a temperature of about 105° C. for about 65 seconds, then to air at a temperature of about 110° C. for about 35 seconds.

EXAMPLE 4

In this instance, the glove formation process was simulated without any post-cure processing to determine the effect of leach time and temperature on the extractable protein level.

After formation of the substrate body as described above, the formers were then dipped into a circulating water bath to leach any residual chemicals and proteins from the substrate body. Fifteen formers were evaluated at each combination of the following conditions: leach times of 2 minutes, 5 minutes, and 8 minutes, and leach temperatures of 45° C., 60° C., and 75° C.

After leaching, the formers were dried at a temperature of about 110° C. for about 67 seconds.

The formers were then dipped into a composition to form the donning layer. The composition included about 2 mass % SYNTHEMUL® 97907-00 silicone-modified vinyl acetate polymer in deionized water. The gloves were then dried for about 67 seconds at a temperature of about 110° C., and stripped from the formers.

The formers were then sent to a curing station having multiple temperature zones to vulcanize and solidify the natural rubber substrate body and the donning layer. The total amount of time required to cure the article was about 30 minutes. The gloves were then easily stripped from the formers.

Figure 4:
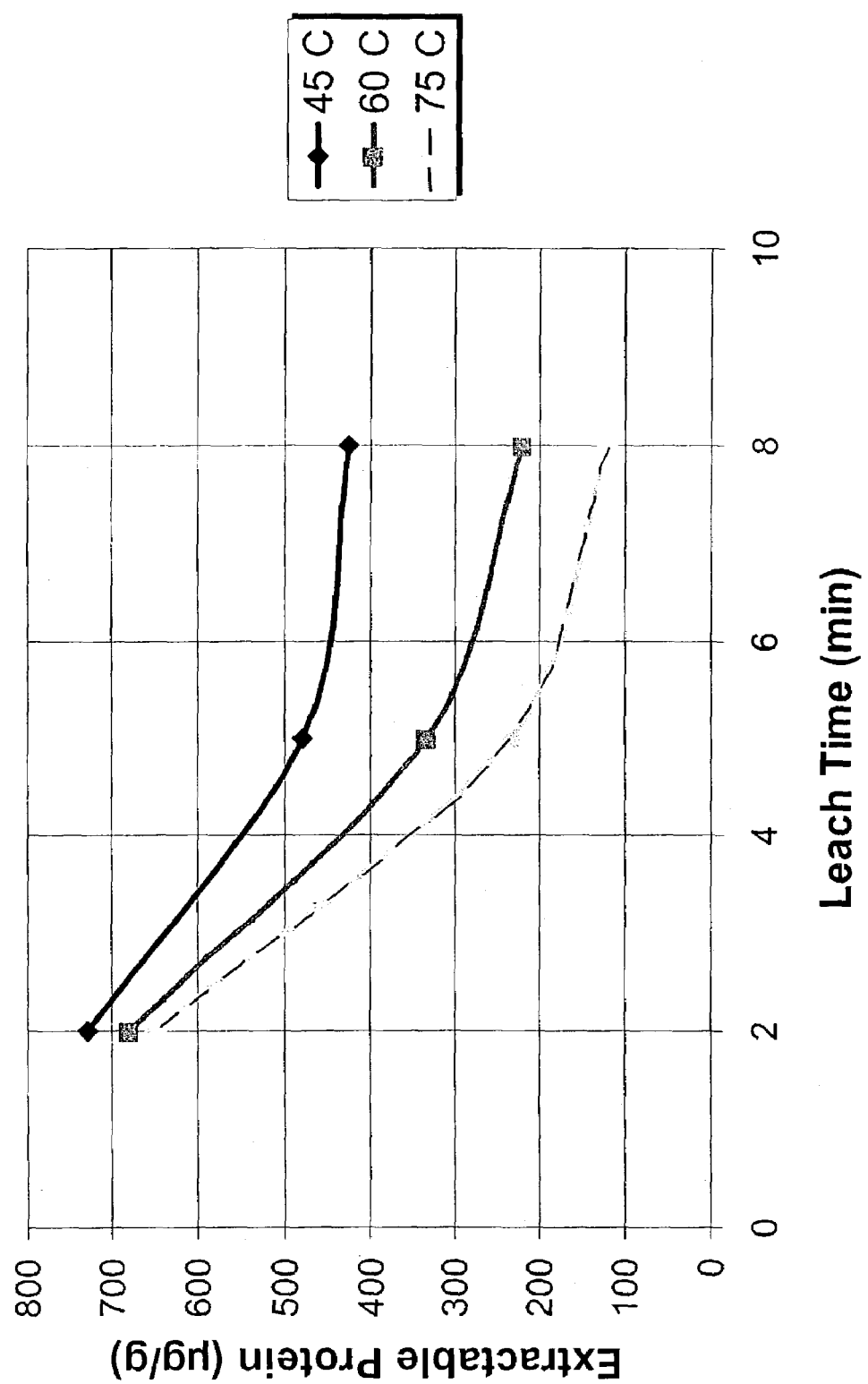
FIG. 4 depicts the amount of extractable protein at various leach times for a glove formed without any post-cure processing.

The gloves were evaluated to determine the residual protein levels using ASTM D5712-95 entitled "Lowry 99 with Background Subtraction". The samples were evaluated at various times and temperatures. The results are presented in FIG. 4. Overall, the extractable protein level decreased as the leach time and leach temperature increased.

EXAMPLE 5

In this instance, a post-cure leaching step was added to determine the impact on the protein reduction.

After formation of the substrate body as described above, the formers were dipped into a circulating water bath to leach any residual chemicals and proteins from the substrate body. The formers were leached for about 2 minutes in water bath was maintained at about 45° C. After leaching, the formers were dried at a temperature of about 110° C. for about 67 seconds.

The formers were then dipped into a composition to form the donning layer. The composition included about 2 mass % SYNTHEMUL® 97907-00 silicone-modified vinyl acetate polymer in deionized water. The formers were then sent to a curing station having multiple temperature zones to vulcanize and solidify the natural rubber substrate body and the donning layer. The total amount of time required to cure the article was about 30 minutes.

The formers were then subject to an additional leaching step. Fifteen formers were evaluated at each combination of the following conditions: leach times of 2 minutes, 5 minutes, and 8 minutes, and leach temperatures of 45° C., 60° C., and 75° C. The gloves were then dried a temperature of about 110° C. for about 67 seconds and easily stripped from the formers.

Figure 5:
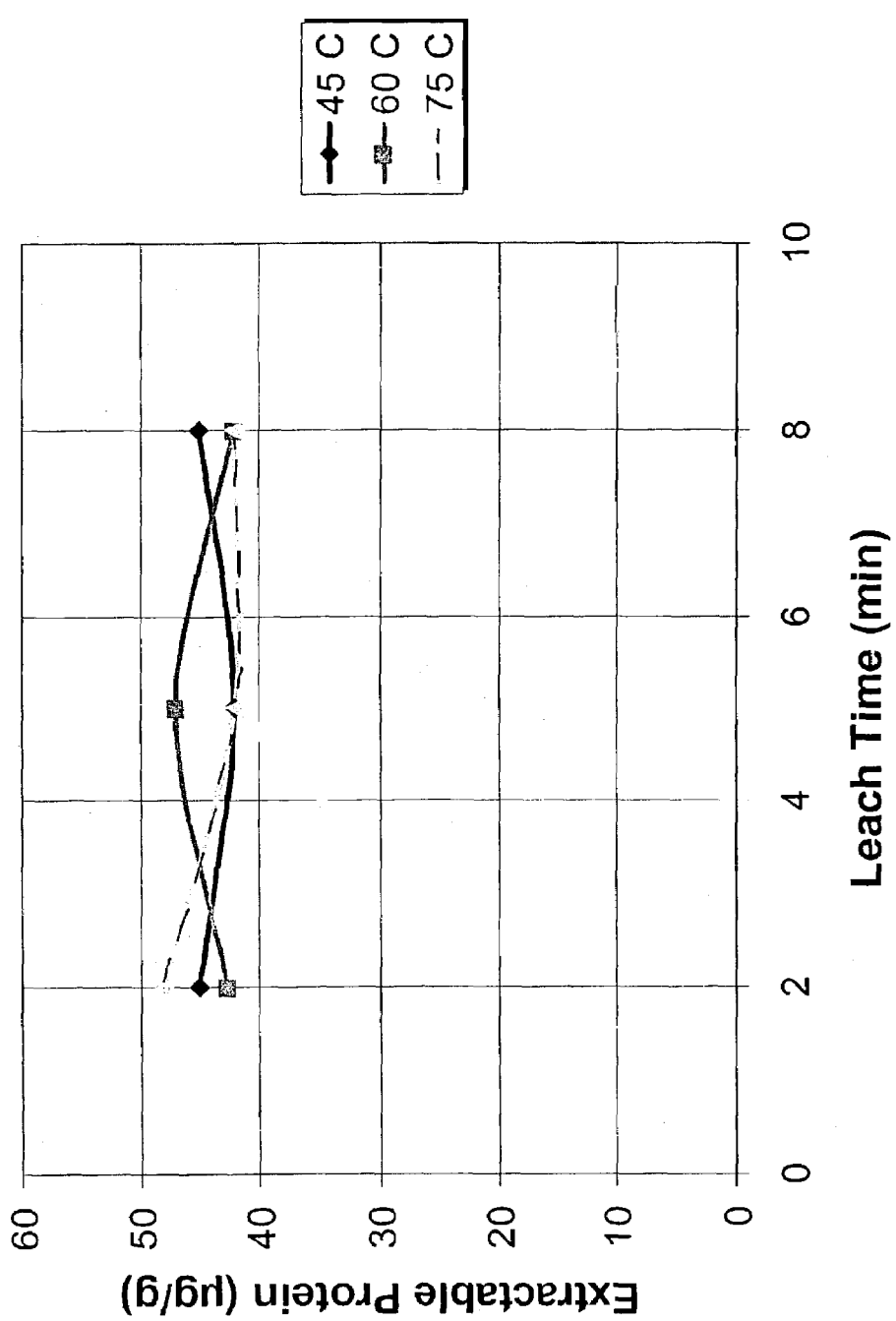
FIG. 5 depicts the amount of extractable protein at various leach times for a glove formed with an additional post-cure leaching step.

The gloves were then evaluated according to ASTM 5712-95 to determine the residual protein levels. The results are presented in FIG. 5. Overall, the extractable protein levels decreased as the leach time and temperature increased. When compared with the gloves made using the process of Example 4, the gloves formed using an additional leaching step had significantly lower extractable protein levels.

EXAMPLE 6

In this instance, the additional leaching step was performed prior to formation of the donning layer over the substrate body.

After formation of the substrate body as described above, the formers were dipped into a circulating water bath to leach any residual chemicals and proteins from the substrate body. The formers were leached for about 2 minutes in a water bath maintained at about 45° C. After leaching, the formers were dried at a temperature of about 110° C. for about 67 seconds.

The formers were then sent to a curing station having multiple temperature zones to vulcanize and solidify the natural rubber substrate body and the donning layer. The total amount of time required to cure the article was about 30 minutes.

The formers were then subject to an additional leaching step. Fifteen formers were evaluated at each combination of the following conditions: leach times of 2 minutes, 5 minutes, and 8 minutes, and leach temperatures of 45° C., 60° C., and 75° C. The gloves were then dried for about 67 seconds at a temperature of about 110° C.

The formers were then dipped into a composition to form the donning layer. The composition included about 4 mass % SYNTHEMUL® 97907-00 silicone-modified vinyl acetate polymer in deionized water. The gloves were then dried for about 67 seconds at a temperature of about 110° C., and easily stripped from the formers.

Figure 6:
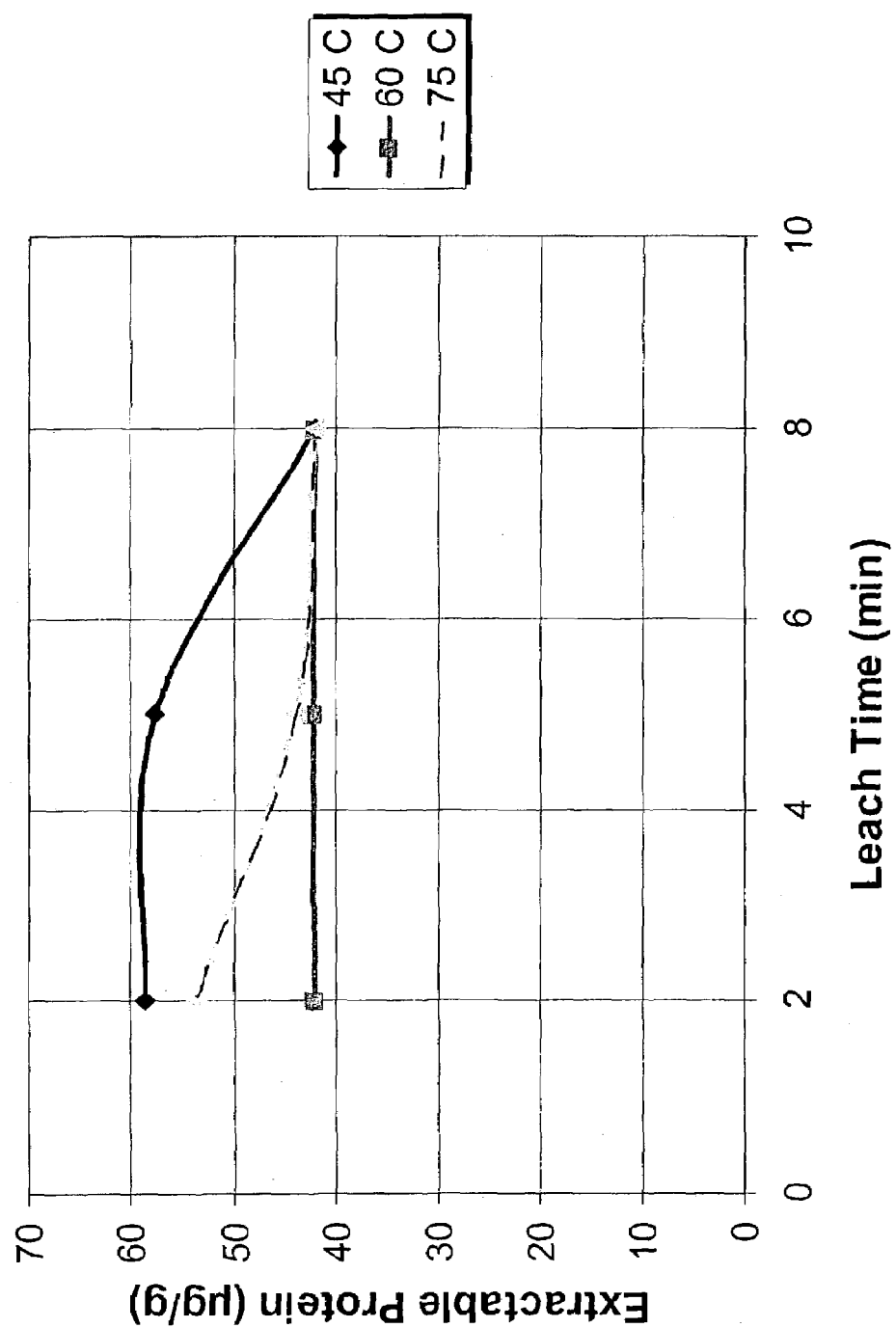
FIG. 6 depicts the amount of extractable protein at various leach times for a glove formed with an additional leaching step performed prior to formation of the donning layer over the substrate body.

The gloves were evaluated according to ASTM 5712-95 to determine the residual protein levels. The results are presented in FIG. 6. Overall, the extractable protein levels decreased as the leach time and temperature increased. When compared with the gloves made using the process of Example 4, the gloves formed using an additional leaching step had a significantly lower extractable protein level. However, when compared with the gloves formed using the process of Example 5, there is little difference between the extractable protein levels. Therefore, while it is beneficial to have a post-formation leaching step, the results indicate that the leaching may occur prior to of after the formation of the donning layer with the same decrease in protein content.

EXAMPLE 7

The ability to form a nitrile butadiene rubber article according to the present invention was demonstrated. In each instance, several glove formers were cleaned and dried. The formers were then dipped into a coagulant composition containing calcium nitrate, a surfactant, and other components. The coagulant on each former was then dried for about 35 seconds at a temperature of about 105° C., and then for about 35 seconds at a temperature of about 75° C.

The formers were then dipped into a composition containing about 30 mass % nitrile rubber in water to form the substrate body of each glove. The formers were then exposed to air to permit the elastomeric material to form a film on the surface of each former. The formers were exposed to air at a temperature of about 105° C. for about 65 seconds, then to air at a temperature of about 110° C. for about 35 seconds.

The substrate body on the former was then leached in circulating water at a temperature of about 45° C. for about 2 minutes to remove any residual coagulant chemicals.

After forming the substrate body as described above, the formers were then dipped into a composition to form the donning layer. The composition included about 1.3 mass % SYNTHEMUL (® 97907-00 silicone-modified vinyl acetate polymer in deionized water.

Each former was then sent to a bead rolling station where a bead was formed on the cuff of each glove. The polymer on the formers was then dried in an oven at about 70° C. for about 20 minutes.

The formers were then sent to a curing station maintained at about 140° C. to vulcanize and solidify the nitrile butadiene rubber substrate body and the donning layer. The total amount of time required to cure the article was about 10 minutes. The gloves were then easily stripped from the formers.

The gloves were then donned to evaluate the efficacy of the silicone-modified vinyl acetate donning layer and found to be readily donned without the use of powder.

In summary, the efficacy of the use of a silicone-modified vinyl acetate polymer as a donning layer and the flexibility of the formation process resulting from its use was demonstrated. Each of the gloves formed in the examples above was readily stripped from the formers and donned without the use of powders. In addition, the donning layer may be formed prior to curing or after curing the article. Furthermore, where a natural rubber article is being formed, the final leaching step may be performed prior to or after formation of the donning layer.

The invention may, be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An elastomeric article comprising:
 a substrate body comprising an elastomeric material, the substrate body having a first surface;
 a donning layer overlying at least a portion of the first surface, the donning layer comprising a silicone-modified vinyl acetate polymer, containing from about 10 atomic % to about 30 atomic % silicon; and
 a lubricant layer overlying at least a portion of the donning layer.

2. The article of claim 1, wherein the elastomeric material comprises natural rubber.

3. The article of claim 1, wherein the elastomeric material comprises a nitrile butadiene rubber.

4. The article of claim 1, wherein the elastomeric material comprises a styrene-ethylene-butylene-styrene block copolymer.

5. The article of claim 1, wherein the elastomeric material is selected from the group consisting of a styrene-isoprene-styrene block copolymer, styrene-butadiene-styrene block copolymer, styrene-isoprene block copolymer, styrene-butadiene block copolymer, synthetic isoprene, chloroprene rubber, polyvinyl chloride, silicone rubber, and a combination thereof.

6. The article of claim 1, wherein the silicone-modified vinyl acetate polymer contains from about 17 atomic % to about 22 atomic % silicon.

7. The article of claim 1, wherein the silicone-modified vinyl acetate polymer contains from about 15 atomic % to about 25 atomic % silicon.

8. The article of claim 1, wherein the lubricant includes at leas one or a combination of the following: a quaternary ammoniun compound; a cationic, anionic, or nonionic, or amphoteric surfactant; a silicone or silicone-based component, and a silicone emulsion.

9. An article comprising a substrate body formed from an elastomeric material, said substrate body having a first surface; and a donning layer comprising a silicone-modified vinyl acetate polymer overlaying at least a portion of said first surface, said silicon-modifed vinyl acetate polymer contains from about 10 atomic % to about 30 atomic % of silicon.

10. The article according to claim 9, wherein said donning layer is non-elastic and does not flake off of said first surface when under stress of being stretched and deformed.

11. The article according to claim 9, wherein said silicone-modifed vinyl acetate polymer contains from about 15 atomic % to about 25 atomic % of silicon.

12. The article according to claim 9, wherein said donning layer is present in am amount of about 0.1 mass % to about 2.5 mass % of said article.

13. The article according to claim 9, wherein said article further includes a lubricating layer overlying at least a portion of said donning layer.

14. The article according to claim 13, wherein said lubricant layer includes, either alone or in combination, at least one of the following: a silicone or silicone-based emulsion, a quaternary ammonium compound, a cationic surfactant, an anionic surfactant, a non-ionic surfactant, or a amphoteric surfactant.

15. The article according to claim 9, wherein said elastomeric material comprises natural rubber.

16. The article according to claim 9, wherein said elastomeric material comprises a nitrile butadiene rubber.

17. The article according to claim 9, wherein said elastomeric material comprises a styrene-ethylene-butylene-styrene (SEBS) block copolymer.

18. The article according to claim 9, wherein said elastomeric material is selected from the group consisting of a styrene-isoprene-styrene block copolymer, styrene-butadiene-styrene block copolymer, styrene-isoprene block copolymer, styrene-butadiene block copolymer, synthetic isoprene, chloroprene rubber, polyvinyl chloride, silicone rubber, and a combination thereof.

19. The article according to claim 9, wherein said article is either a glove or a condom.

* * * * *